(12) United States Patent
Fago

(10) Patent No.: US 12,714,429 B2
(45) Date of Patent: Aug. 25, 2026

(54) CURVED DUAL SIDE SPRING V-CLIP FOR SURGICAL TREATMENT OF LEFT ATRIAL APPENDAGE

(71) Applicant: AtriCure, Inc., Mason, OH (US)

(72) Inventor: Frank Fago, Mason, OH (US)

(73) Assignee: AtriCure, Inc., Mason, OH (US)

( * ) Notice: Subject to any disclaimer, the term of this patent is extended or adjusted under 35 U.S.C. 154(b) by 397 days.

(21) Appl. No.: 18/464,121

(22) Filed: Sep. 8, 2023

(65) Prior Publication Data

US 2025/0082331 A1 Mar. 13, 2025

(51) Int. Cl.

| | |
|---|---|
| ***A61B 17/12*** | (2006.01) |
| ***A61B 17/00*** | (2006.01) |
| ***A61B 17/122*** | (2006.01) |
| ***A61B 17/128*** | (2006.01) |

(52) U.S. Cl.

CPC .. *A61B 17/12022* (2013.01); *A61B 17/00234* (2013.01); *A61B 17/1227* (2013.01); *A61B 17/1285* (2013.01); *A61B 2017/00243* (2013.01); *A61B 2017/1205* (2013.01)

(58) Field of Classification Search

CPC ........ A61B 17/12022; A61B 17/00234; A61B 17/1227; A61B 17/1285; A61B 2017/00243; A61B 2017/1205; A61B 17/128; A61B 17/122; A61B 17/1222; A61B 17/08; A61B 17/083; A61B 17/10; A61B 2017/00575; A61B 2017/00584; Y10T 24/44376; Y10T 24/44385; Y10T 24/4441; Y10T 24/44479

See application file for complete search history.

(56) References Cited

U.S. PATENT DOCUMENTS

| | | |
|---|---|---|
| 7,645,285 B2 | 1/2010 | Cosgrove et al. |
| 7,931,578 B2 | 4/2011 | Whayne et al. |
| 8,465,507 B2 | 6/2013 | Cosgrove et al. |

(Continued)

FOREIGN PATENT DOCUMENTS

| | | |
|---|---|---|
| WO | WO 2023/039574 | 3/2023 |

OTHER PUBLICATIONS

U.S. Appl. No. 16/536,936, filed Aug. 9, 2019, Privitera et al.

(Continued)

*Primary Examiner* — Kathleen S Holwerda
*Assistant Examiner* — James R McGinnity
(74) *Attorney, Agent, or Firm* — Levine Bagade Han LLP

(57) ABSTRACT

A clip and method provide for surgically minimizing or eliminating an atrial appendage of the patient using a clip. The curved side spring V-clip includes first and second elongate beams having matching distally curved portions. The clip includes a dual side springs configured to urge the first and the second elongate beams from an open V-shaped position to a parallel closed position. Right-side spring and left-side spring have first and second terminal ends attached to distal sections respectively of the first and the second elongate beams. The right and the left-side springs extend proximally to a respective proximal bend. The V-clip is configured to resist lateral splaying movement of the first and the second elongate beams. by including one or more of a lateral spacing element attached between respective proximal bends of the right and the left-side spring or having springs of different strengths.

16 Claims, 8 Drawing Sheets

(56) References Cited

U.S. PATENT DOCUMENTS 8,636,754 B2 1/2014 Hughett et al.
8,715,302 B2 5/2014 Ibrahim et al.
8,814,778 B2 8/2014 Kiser et al.
8,852,218 B2 10/2014 Hughett et al.
8,945,151 B2 2/2015 Salas
9,017,349 B2 4/2015 Privitera et al.
9,119,627 B2 9/2015 Cosgrove et al.
9,265,486 B2 2/2016 Hughett et al.
9,282,973 B2 3/2016 Hughett et al.
9,393,023 B2 7/2016 Privitera et al.
9,463,024 B2 10/2016 Kiser et al.
9,861,371 B2 1/2018 Martin et al.
9,883,863 B2 2/2018 Hughett et al.
9,883,867 B2 2/2018 Martin et al.
9,888,925 B2 2/2018 Bertolero et al.
9,901,352 B2 2/2018 Fago et al.
10,098,640 B2 10/2018 Bertolero et al.
10,166,024 B2 1/2019 Williamson et al.
10,182,823 B2 1/2019 Miller
10,182,824 B2 1/2019 Monti et al.
10,238,398 B2 3/2019 Hughett et al.
10,278,704 B2 5/2019 Kiser et al.
10,285,712 B2 5/2019 Cosgrove et al.
10,314,585 B2 6/2019 Williamson et al.
10,426,475 B2 10/2019 Privitera et al.
10,433,854 B2 10/2019 Miller et al.
10,524,791 B2 1/2020 Bertolero et al.
10,631,874 B2 4/2020 Martin et al.
10,758,243 B2 9/2020 Salas
10,869,668 B2 12/2020 Privitera et al.
10,898,204 B2 1/2021 Winkler et al.
10,918,392 B2 2/2021 Deville et al.
11,191,547 B2 12/2021 Deville et al.
11,266,413 B2 * 3/2022 Winkler ........... A61B 17/12099
11,284,899 B2 3/2022 Ibrahim et al.
11,324,510 B2 5/2022 Morejohn et al.
12,446,892 B2 * 10/2025 Fago .................. A61B 17/1227
2019/0357912 A1 11/2019 Privitera et al.
2021/0038226 A1 2/2021 Bales et al.
2021/0106336 A1 4/2021 Winklier et al.
2022/0361886 A1 11/2022 Widenhouse et al.
2023/0009892 A1 1/2023 Winklier et al.
2023/0023804 A1 1/2023 Hughett et al.
2023/0083170 A1 3/2023 Biehle et al.
2023/0083697 A1 3/2023 Recker et al.
2023/0083738 A1 3/2023 Ziton et al.
2023/0087254 A1 3/2023 Seith et al.
2023/0255637 A1 * 8/2023 Scholten ............ A61B 17/1227 606/151
2025/0082339 A1 3/2025 Fago

OTHER PUBLICATIONS

U.S. Appl. No. 17/131,975, filed Dec. 23, 2020, Winklier et al.
U.S. Appl. No. 17/676,516, filed Feb. 21, 2022, Winkler et al.
U.S. Appl. No. 17/875,582, filed Jul. 28, 2022, Widenhouse et al.
U.S. Appl. No. 17/931,305, filed Mar. 16, 2023, Mata et al.
U.S. Appl. No. 17/931,309, filed Sep. 12, 2022, Recker et al.
U.S. Appl. No. 17/931,316, filed Sep. 12, 2022, Ziton et al.
U.S. Appl. No. 17/931,324, filed Sep. 12, 2023, Biehle et al.
U.S. Appl. No. 17/958,347, filed Oct. 1, 2022, Hughett et al.
U.S. Appl. No. 18/464,114, filed Sep. 8, 2023, Fago.

* cited by examiner

CURVED DUAL SIDE SPRING V-CLIP FOR SURGICAL TREATMENT OF LEFT ATRIAL APPENDAGE

CROSS-REFERENCE TO RELATED APPLICATIONS

The present application is related to co-pending application U.S. patent application Ser. No. 18/464,144 filed on Sep. 8, 2023 as the present application by inventor Frank Fago. The co-pending application is thereby incorporated herein by reference.

FIELD OF THE INVENTION

The present disclosure is directed to implantable medical devices, and, more specifically, to implantable exclusion devices for anatomical structures, and related instruments and related methods.

BACKGROUND OF THE INVENTION

The present disclosure contemplates that atrial fibrillation is a common heart arrhythmia, affecting millions of people in the United States. In some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA using an occlusion device. Generally known LAA clips are surgically implanted concomitant with other open thoracic surgical procedures such as coronary artery bypass graft surgery (CABG).

SUMMARY OF THE INVENTION

According to one aspect of the present disclosure, an apparatus such as an occlusion clip is provided for eliminating or mitigating a tissue appendage of a patient. The apparatus includes a first elongate beam having a straight proximal portion and laterally curved distal portion. The apparatus includes a second elongate beam that matches the first elongate beam and that is positionable between a closed state in parallel alignment with the first elongate beam and an open state being distally angled away from the first elongate beam in a V-shape. The apparatus includes a dual side spring assembly that is configured to urge the first and the second elongate beams from the open position to the closed position. The dual side spring assembly includes a right-side spring and a left-side spring having first and second terminal ends attached to distal sections respectively of the first and the second elongate beams and extending proximally to a respective proximal bend. The dual side spring assembly includes a lateral spacing element attached between respective proximal bends of the right and the left-side spring that maintains parallel alignment to resist lateral splaying movement of the first and second elongate beams.

According to another aspect of the present disclosure, an apparatus such as an occlusion clip is provided for eliminating or mitigating a tissue appendage of a patient. In one or more embodiments, the apparatus includes a first elongate beam having a straight proximal portion and laterally curved distal portion that defines a concave lateral side and a convex lateral side. The apparatus includes a second elongate beam that matches the first elongate beam and that is positionable between a closed state in parallel alignment with the first elongate beam and an open state being distally angled away from the first elongate beam in a V-shape. The apparatus includes a right-side spring having a first cross sectional dimension and having first and second terminal ends attached to distal sections respectively of the first and the second elongate beams and extending proximally to a respective proximal bend. The apparatus includes a left-side spring having a second cross sectional dimension that is different from the first cross sectional dimension and having first and second terminal ends attached to distal sections respectively of the first and the second elongate beams and extending proximally to a respective proximal bend, one of the right and the left-side springs having a larger one of the first and the second cross sectional dimension being on the concave lateral side.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 8 is a side view of the example curved dual side spring V-clip of FIG. 5 in a closed position, according to one or more embodiments;

DETAILED DESCRIPTION

Figure 1A:
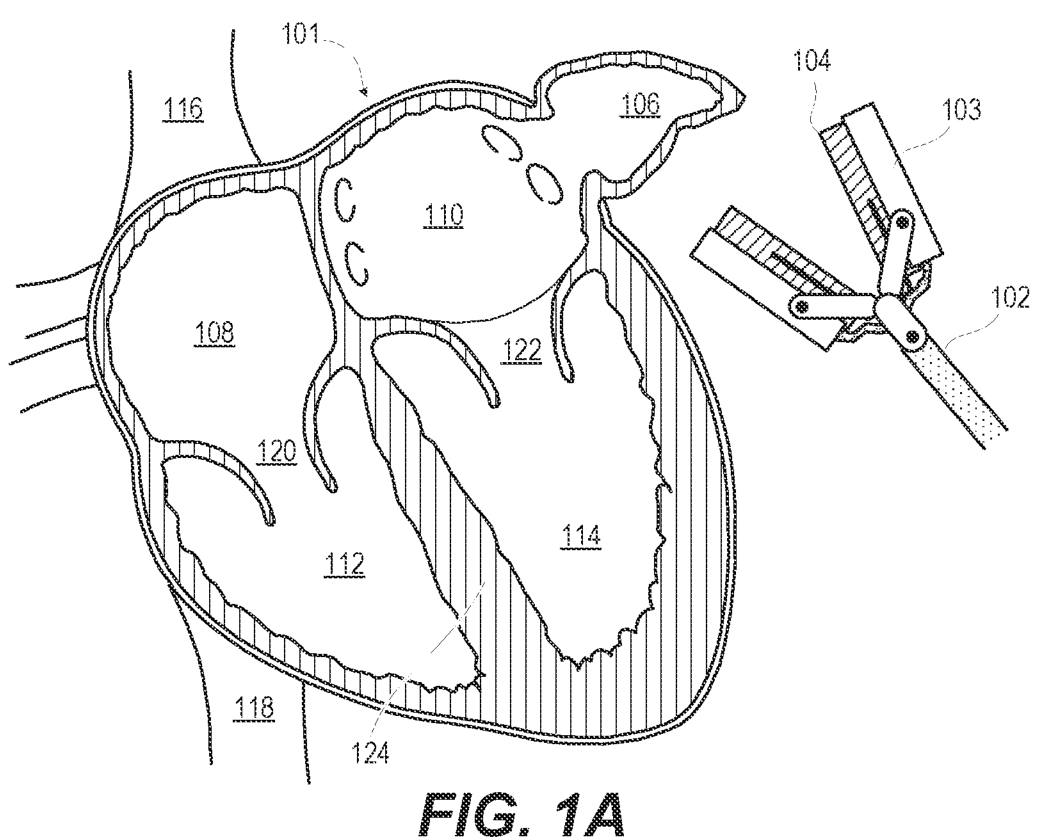
FIG. 1A is a cross section view of a human heart that is being approached by a curved V-clip applier having an end effector in an open position that holds a curved dual side spring V-clip for treatment of a left atrial appendage (LAA) to prevent certain types of ischemic stroke, according to one or more embodiments.

According to aspects of the present disclosure, a curved dual side spring V-clip and method provide for surgically minimizing or eliminating an atrial appendage of the patient using the V-clip. The clip includes first and second elongate beams. The clip includes a curved dual side spring assembly configured to urge the first and the second elongate beams from an open V-shaped position to a parallel closed position. The first and the second elongate beams having aligned shapes that distally curve to one lateral side, forming a convex side and a concave side. The dual side spring assembly includes a right-side spring and a left-side spring having first and second terminal ends attached to distal sections respectively of the first and the second elongate beams. The right and the left-side springs extend proximally to a respective proximal bend. To resist lateral splaying movement of the first and the second elongate beams, the right-side and left-side springs are configured with one or more of: (i) a lateral spacing element attached between respective proximal bends of the right and the left-side spring that maintains parallel alignment; (ii) a stronger one of the right and the left-side springs that is on the concave side of the first and the second elongate beams; and (iii) a shorter one of the right and the left-side springs that is on the concave side of the first and the second elongate beams.

In the following detailed description of exemplary embodiments of the disclosure, specific exemplary embodiments in which the various aspects of the disclosure may be practiced are described in sufficient detail to enable those skilled in the art to practice the invention, and it is to be understood that other embodiments may be utilized and that logical, architectural, programmatic, mechanical, electrical, and other changes may be made without departing from the spirit or scope of the present disclosure. The following detailed description is, therefore, not to be taken in a limiting sense, and the scope of the present disclosure is defined by the appended claims and equivalents thereof. Within the descriptions of the different views of the figures, similar elements are provided similar names and reference numerals as those of the previous figure(s). The specific numerals assigned to the elements are provided solely to aid in the description and are not meant to imply any limitations (structural or functional or otherwise) on the described embodiment. It will be appreciated that for simplicity and clarity of illustration, elements illustrated in the figures have not necessarily been drawn to scale. For example, the dimensions of some of the elements are exaggerated relative to other elements.

It is understood that the use of specific component, device and/or parameter names, such as those of the executing utility, logic described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

As further described below, implementation of the functional features of the disclosure described herein is provided within processing devices and/or structures and can involve use of a combination of hardware, that execute to provide a specific utility for the device or a specific functional logic. The presented figures illustrate hardware components.

Those of ordinary skill in the art will appreciate that the hardware components and basic configurations depicted in the figures may vary. The illustrative components are not intended to be exhaustive, but rather are representative to highlight essential components that are utilized to implement aspects of the described embodiments. For example, other devices/components may be used in addition to or in place of the hardware depicted. The depicted example is not meant to imply architectural or other limitations with respect to the presently described embodiments and/or the general invention. The description of the illustrative embodiments can be read in conjunction with the accompanying figures. Embodiments incorporating teachings of the present disclosure are shown and described with respect to the figures presented herein.

FIG. 1A is a cross section view of a human heart 101 that is being approached by an applier mechanism or V-clip applier 102 having an end effector 103 in an open position that holds a curved side spring V-clip 104 for treatment of a left atrial appendage (LAA) 106 to prevent certain types of stroke. The V-clip applier 102 in one or more embodiments can separate the curved side spring V-clip 104 to a V-shaped acute angle as depicted. As depicted below in FIG. 9, in one or more embodiments, a V-clip applier 102 can open the curved side spring V-clip 104 with a parallel spacing in a U-shape. For simplicity, the curved side spring V-clip 104 is described as having a V-shape merely to connote having an open side. The side spring V-clip 104 can be an apparatus for occluding the LAA 106. The human heart 101 has four chambers: (i) right atria (RA) 108; (ii) left atria (LA) 110; (iii) right ventricle (RV) 112; and left ventricle (LV) 114. The RA 108 receives blood from the venous vasculature. Venous blood enters the RA 108 from the superior vena cava (SVC) blood vessel 116 and the inferior vena cava (IVC) blood vessel 118. Normal pumping of the heart 101 causes blood in the RA 108 to flow through the tricuspid valve (TV) 120 into the right ventricle (RV) 112. Blood in the RV 112 is expelled from the heart 101 into the pulmonary artery. Blood expelled into the pulmonary artery flows into the lungs where the blood is oxygenated and thereafter flows back to the LAA 106. The oxygenated blood in the LA 110 flows through the mitral valve (MV) 122 into the LV 114. Blood in the LV 114 is then expelled out of the heart 101 into the ascending aorta and from there to smaller vessels of the systemic circulation. A wall of the heart 101, referred to as a septum 124, separates right and left sides of the heart 101. The RA 108 and LA 110 are separated by an upper atrial portion of the septum 124. The RV 112 and LV 114 are separated by a lower thicker ventricular portion of the septum 124. The LAA 106 extends off of the LA 110 and is a blind-ended structure.

Figure 1B:
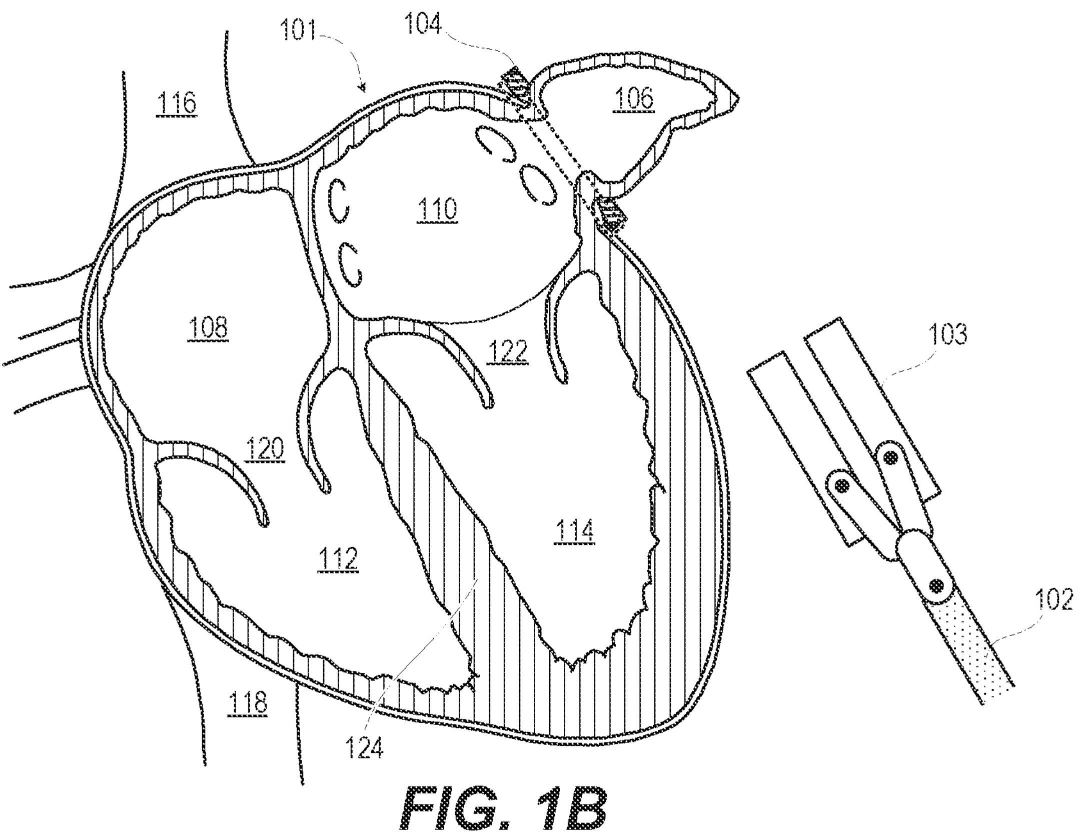
FIG. 1B is a cross section of the human heart after dispensing of the curved dual side spring V-clip by the V-clip applier, according to one or more embodiments.

FIG. 1B is a cross section of the human heart 101 after dispensing of the side spring V-clip 104 by the V-clip applier 102. The end effector 103 of the V-clip applier 102 can be in a closed position, reducing the size of the end effector 103 for retraction from the patient. The clip 104 closed on the LAA 106 can eliminate or minimize the LAA 106 to reduce stroke risk among other benefits. Aspects of the present disclosure provide an alternative biasing approach for the clip and dispenser as disclosed for example in U.S. Pat. No. 8,852,218, the disclosure of which is hereby incorporated by reference in its entirety to the extent compatible with the teaching herein.

Figure 2:
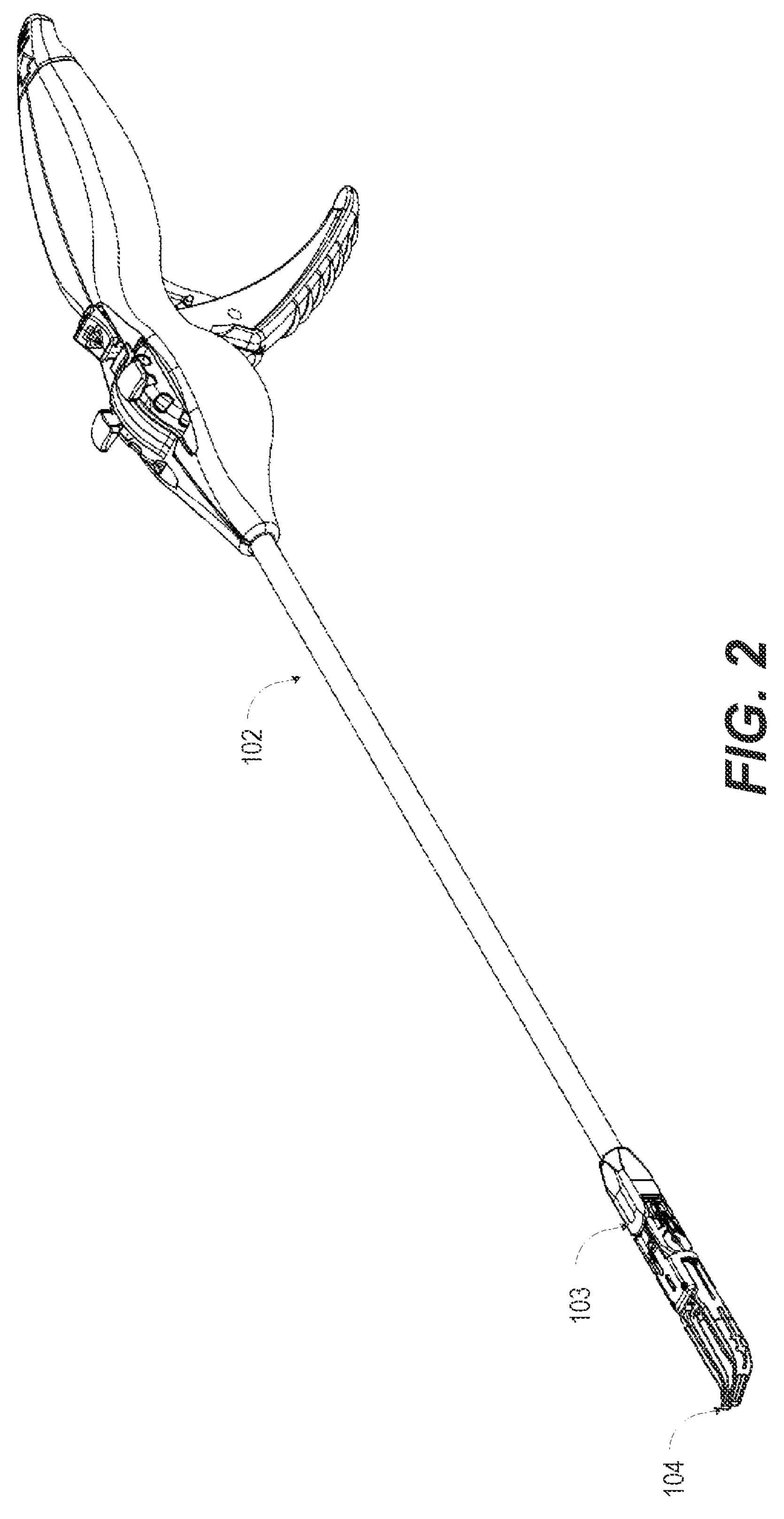
FIG. 2 is a three-dimensional view of the curved dual side spring V-clip applier with an end effector holding the curved dual side spring V-clip, according to one or more embodiments.

FIG. 2 is a three-dimensional view of the V-clip applier 102 with an end effector 103 holding the curved dual side spring V-clip 104. In this example, the V-clip applier 102 can be similar or identical to embodiments disclosed in U.S. Pat. No. 9,883,867 B2, the disclosure of which is hereby incorporated by reference in its entirety. The end effector 103 can be shaped to engage curved dual side spring V-clip 104.

Figure 3:
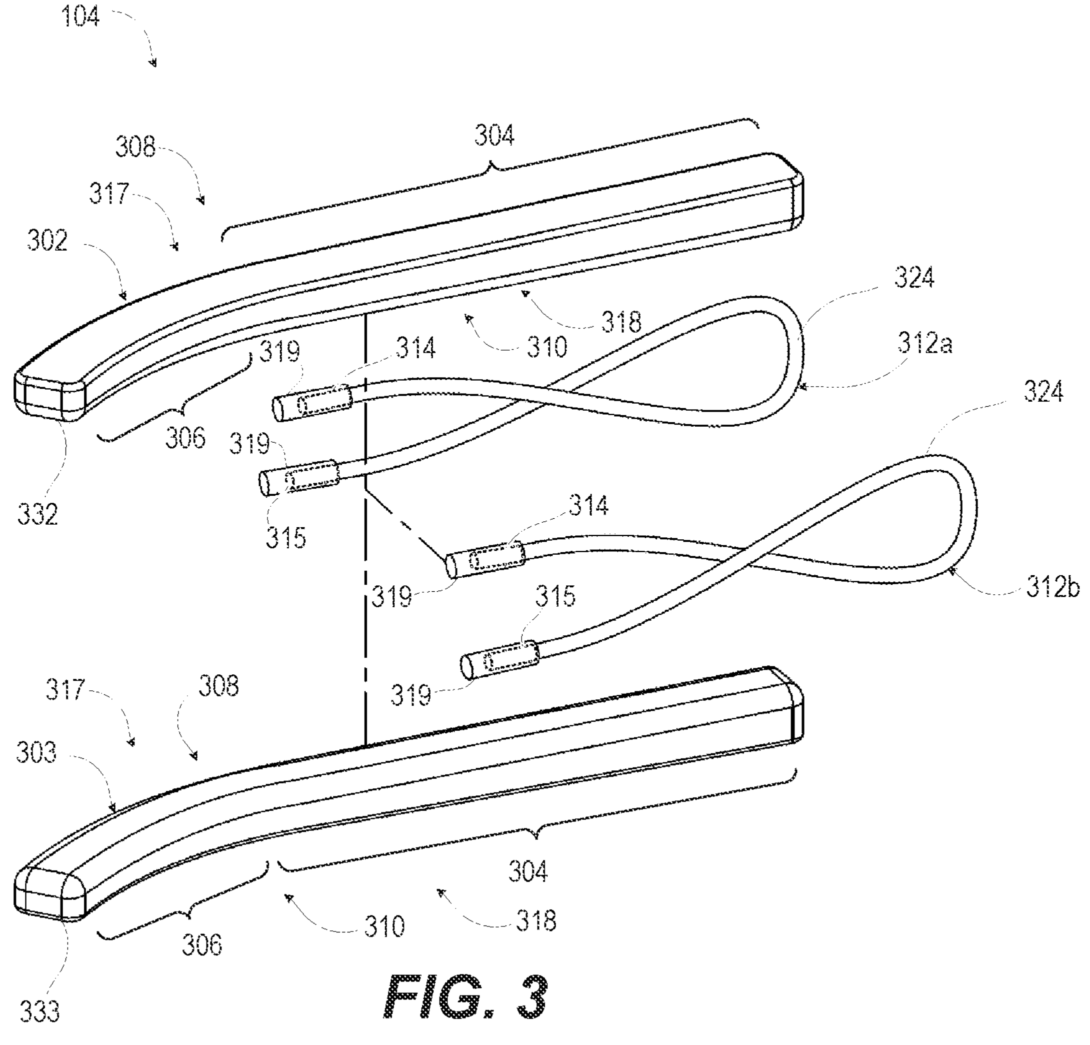
FIG. 3 is a three-dimensional exploded view of an example curved dual side spring V-clip having a lateral spacing element to maintain parallel alignment of side springs, preventing splaying apart after deployment, according to one or more embodiments.

FIG. 3 is a three-dimensional exploded view of an example curved dual side spring V-clip 104 that can include a first elongate beam 302 and a second elongate beam 303. As depicted, the first elongate beam 302 can be vertically above the second elongate beam 303 that matches the first elongate beam 302. A long dimension of the first elongate beam 302 and the second elongate beam 303 can be generally along a longitudinal axis. Specifically, a straight proximal portion 304 respectively of each of the first elongate beam 302 and the second elongate beam 303 can be aligned with the longitudinal axis. Each can include a laterally curved distal portion 306 that diverges to one lateral side from the longitudinal axis, defining a convex side 308 depicted in an example as a right side 317, and defining a concave side 310 depicted in the example as a left-side 318. The second elongate beam 303 that matches the first elongate beam 302 can be positionable between a closed state in parallel alignment with the first elongate beam 302 and an open state being distally acutely angled away or in parallel spaced away from the first elongate beam 302 in a V-shape or a U-shape, respectively. A right-side spring 312*a* and a left-side spring 312*b* can respectively comprise a first terminal end 314 and a second terminal end 315 attached at about the midpoint respectively to right side 317 and left side 318 of the first elongate beam 302 and the second elongate beam 303. The first terminal end 314 and the second terminal end 315 of the right-side spring 312*a* and the left-side spring 312*b* can be received within an overmolded portion 319 of a corresponding first elongate beam 302 and second elongate beam 303 as described below with regard to FIGS. 11A-11G. Each of the right-side spring 312*a* and the left-side spring 312*b* can extend proximally to a respective proximal bend 324.

Figure 4:
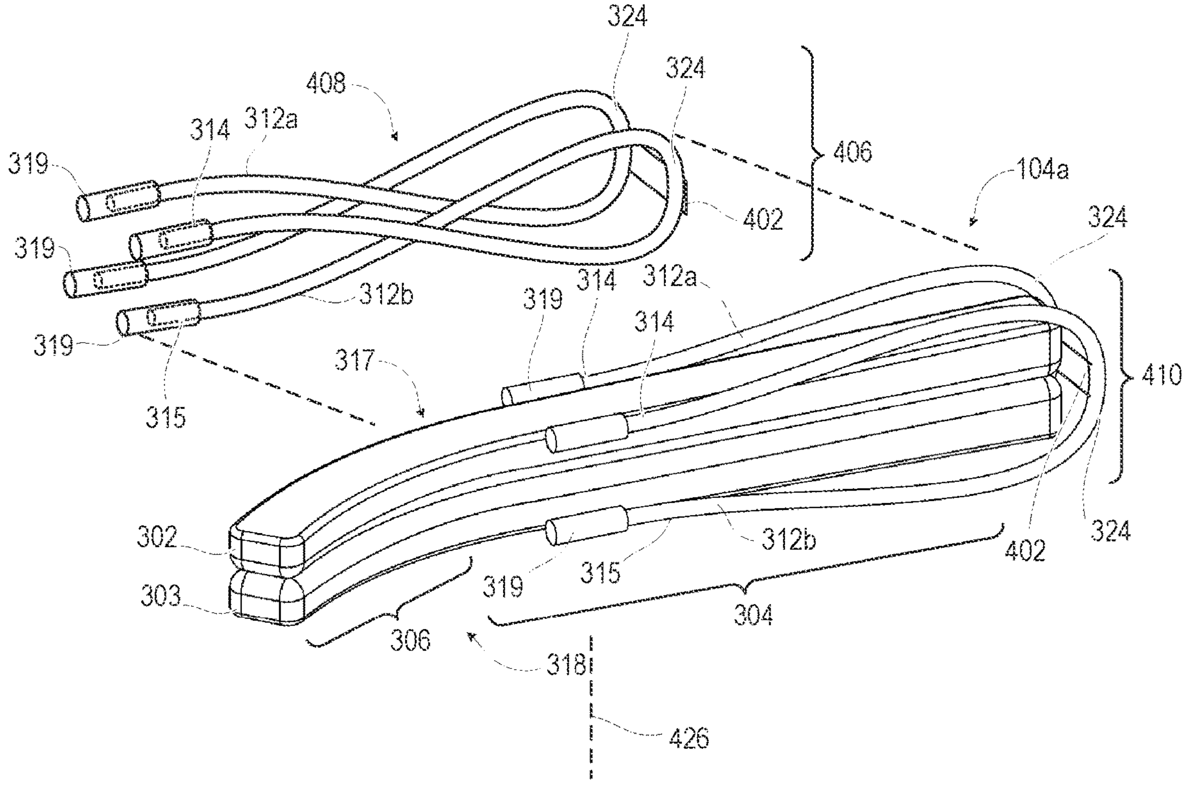
FIG. 4 is a three-dimensional exploded view of another example curved dual side spring V-clip having a lateral spacing element to maintain parallel alignment of side springs, preventing splaying apart after deployment, according to one or more embodiments.
Figures 5, 6, 7:
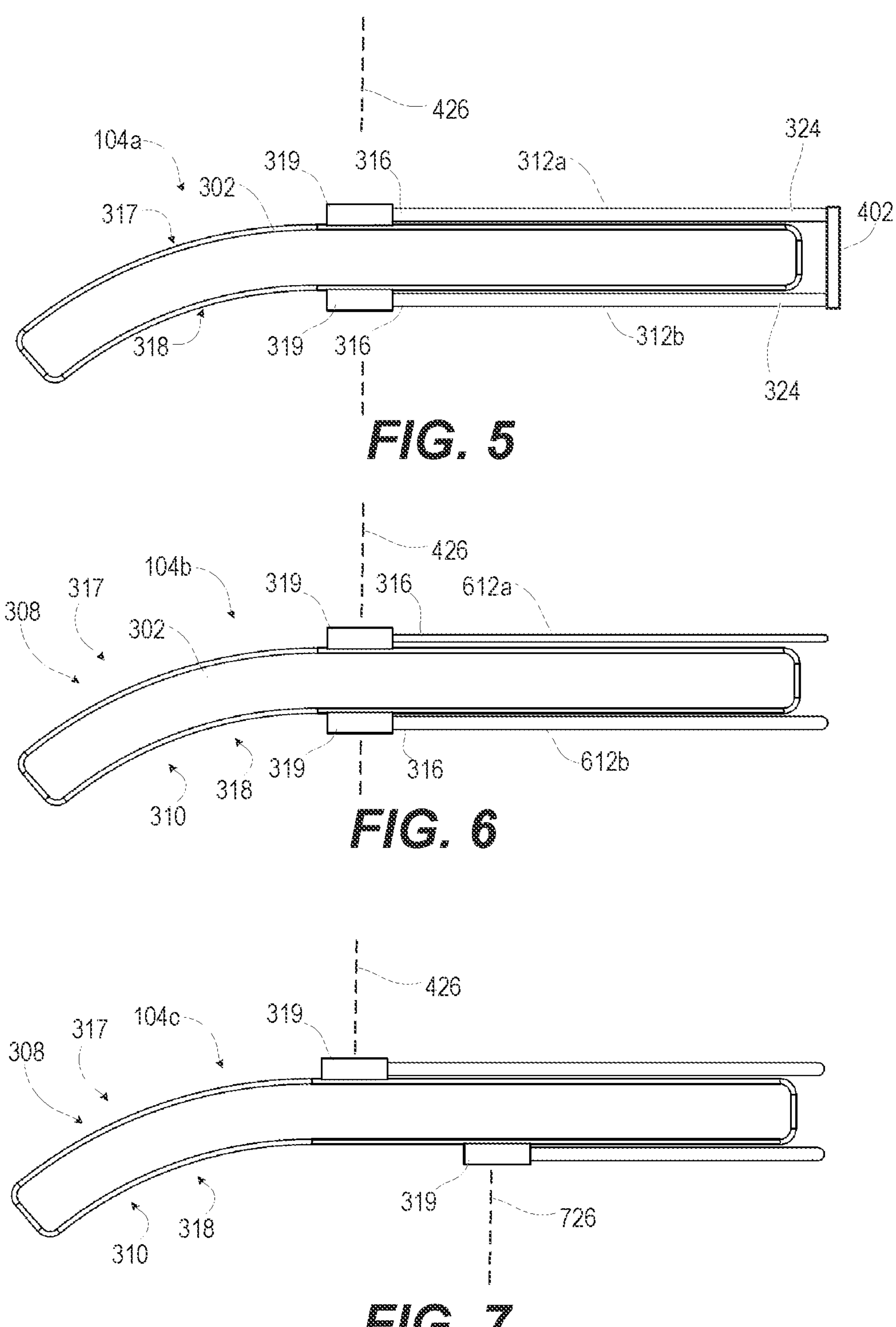
FIG. 5 is a top view of the example curved dual side spring V-clip of FIG. 4 having laterally aligned spring attachments to beams, according to one or more embodiments.
FIG. 6 is a top view of an alternative curved dual side spring V-clip having different diameter springs to reduce splaying of the elongate beams after deployment, according to one or more embodiments.
FIG. 7 is a top view of an alternative curved dual side spring V-clip having longitudinally displaced spring attachments to beams to reduce splaying of the elongate beams after deployment, according to one or more embodiments.

Aspects of the present disclosure described below provide modifications or additions the curved side spring V-clip 104 to maintain matching alignment and to resist splaying movement of the first elongate beam 302 and the second elongate beam 303 after deployment. In one example, FIG. 4 is a three-dimensional view of an example dual side spring V-clip 104*a* having a lateral spacing element 402 to prevent splaying apart of the right-side spring 312*a* and the left-side spring 312*b* after deployment. FIG. 5 is a top view of the example dual side spring V-clip 104*a* having the lateral spacing element 402 between the right-side spring 312*a* and the left-side spring 312*b* that are of the same longitudinal length and strength. With particular reference to FIG. 4, at 406, a dual side spring assembly 408 stabilized by lateral spacing element 431402 is depicted with the right-side spring 312*a* and the left-side spring 312*b* in a relaxed state. At 410, the stabilized side spring assembly 408 can be attached to other components of the dual side spring V-clip 104*a*. In one or more embodiments, the dual side spring V-clip 104*a* can provide as clamping members the first elongate beam 302 and the second elongate beam 303 as described above for FIG. 3.

When detached at 406, the right-side spring 312*a* and the left-side spring 312*b* can relax to a crossed single coil spring position. When attached at 410, from first terminal end 314 and second terminal end 315, the right-side spring 312*a* and the left-side spring 312*b* can extend proximally to a respective proximal bend 324, forming generally a two-dimensional bulb shape The lateral spacing element 402 can be attached between respective proximal bends 324 of the right-side spring 312*a* and the left-side spring 312*b* to maintain parallel alignment and thus to resist lateral splaying movement of the first elongate beam 302 and the second elongate beam 303 of the dual side spring V-clip 104. The first terminal end 314 and the second terminal end 315 of the right-side spring 312*a* can be vertically aligned at a first longitudinal position 426 on right-sides 317 respectively of the first elongate beam 302 and the second elongate beam 303. The first terminal end 314 and the second terminal end 315 of the left-side spring 312*b* can be vertically aligned at the first longitudinal position 426 on left-sides 318 respectively of the first elongate beam 302 and the second elongate beam 303. The right-side spring 312*a* and the left-side spring 312*b* can be identically sized as depicted in FIGS. 3-4.

The first elongate beam 302 and the second elongate beam 303 can comprise atraumatic inward surfaces 332, 333. The geometry of the clamping portion interface between the clip beam and the appendage can be atraumatic. Patients that require the V-clip 104 already can have compromised cardiac systems so the appendage may be friable. Accordingly, the clip 104 can comprise a contact surface that does not create stress concentrations that could abrade or cut the appendage.

Additional information is provided in the commonly owned U.S. patent application Ser. No. 17/931,309 filed on 12 Sep. 2022 and entitled "Exclusion Device Beams and Related Methods", the disclosure of which is hereby incorporated by reference in its entirety. In particular, more detail is provided regarding beam shape and surface texture possibilities. The atraumatic clamping surface texture does not tend to abrade the beating heart especially with direct contact to the tissue.

In one or more embodiments, the clip 104 can have a texture that is intended to interface with a knit braided polyester fabric cover to increase friction and keep the clip in place until the tissue grows into the fabric and clip. The polyester cover can provide a smooth uniform contact area that minimizes trauma to the appendage. The first elongate beam 302 and the second elongate beam 303 can include or be wholly composed of one or more materials compatible with surgical implantation on a left atrial appendage of a heart of a patient.

In one or more embodiments, the right-side spring 312*a* and the left-side spring 312*b* can each have a round spring design and are maintained in parallel alignment by the lateral spacing element 402 to ensure that the clamping members, depicted as first elongate beam 302 and second elongate beam 303 are lined up with each other to transfer force to the appendage (LA 110 of FIG. 1A). If the clamping members are not lined up, the round side springs can not apply a restoring lateral force due to alignment provided by the lateral spacing element 402. By maintaining parallel alignment of right-side spring 312*a* and the left-side spring 312*b*, first elongate beam 302 and second elongate beam 303 can comprise consistent force along the length of the beams and may not exclude the appendage completely.

FIG. 6 is a top view of an alternative curved dual side spring V-clip 104*b* having different diameter right-side spring 612*a* and left-side spring 612*b* to reduce splaying of the first elongate beam 302 and the second elongate beam 303 after deployment. The right-side spring 612*a* can have a first cross sectional dimension and the left-side spring 612*b* having a second cross sectional dimension that is different from the first cross sectional dimension. One of the right-side spring 612*a* and the left-side spring 612*b* can have a larger one of the first and the second cross sectional dimensions being on the concave side 310, which is depicted as the left-side 318.

FIG. 7 is a top view of an alternative dual side spring V-clip 104*c* having longitudinally displaced spring attachments to the first and the second elongate beams 302 and 303 (FIG. 3) to resist splaying movement. The first terminal end 314 and the second terminal end 315 (FIG. 3) of the right-side spring 312*a* can be vertically aligned at the first longitudinal position 426 on right-sides 317 respectively of the first elongate beam 302 and the second elongate beam 303 (FIG. 3). The first and the second terminal ends 314 and 315 (FIG. 3) of the left-side spring 312*a* can be vertically aligned at a second longitudinal position 726 on left-sides 318 respectively of the first elongate beam 302 and the second elongate beam 303. The second longitudinal position 726 can be longitudinally spaced from the first longitudinal position 426. The right-side spring 312*a* and the left-side spring 312*b* can be sized differently or identically. In some embodiments, the left-side spring 312*b* can be longitudinally shorter than the right-side spring 312*a*.

Figure 9:
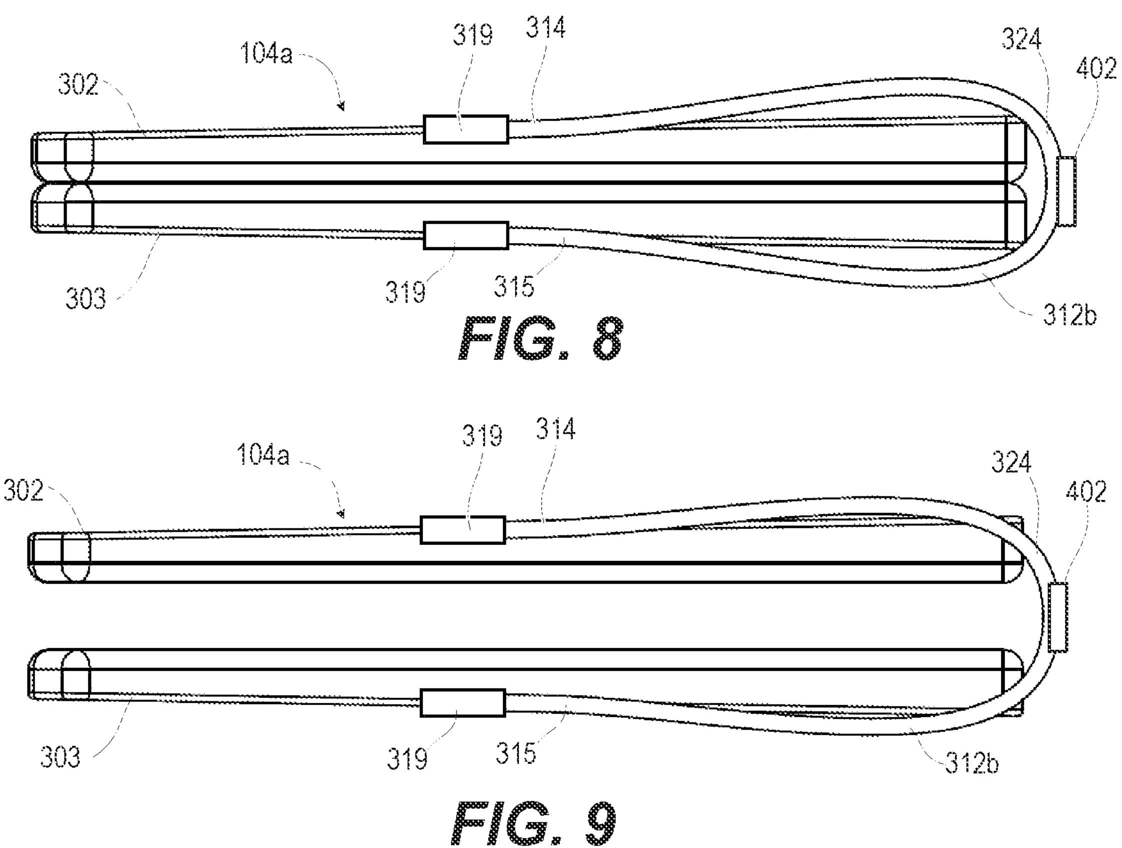
FIG. 9 is a side view of the example curved dual side spring V-clip of FIG. 5 in a partially open position, according to one or more embodiments.
Figure 10:
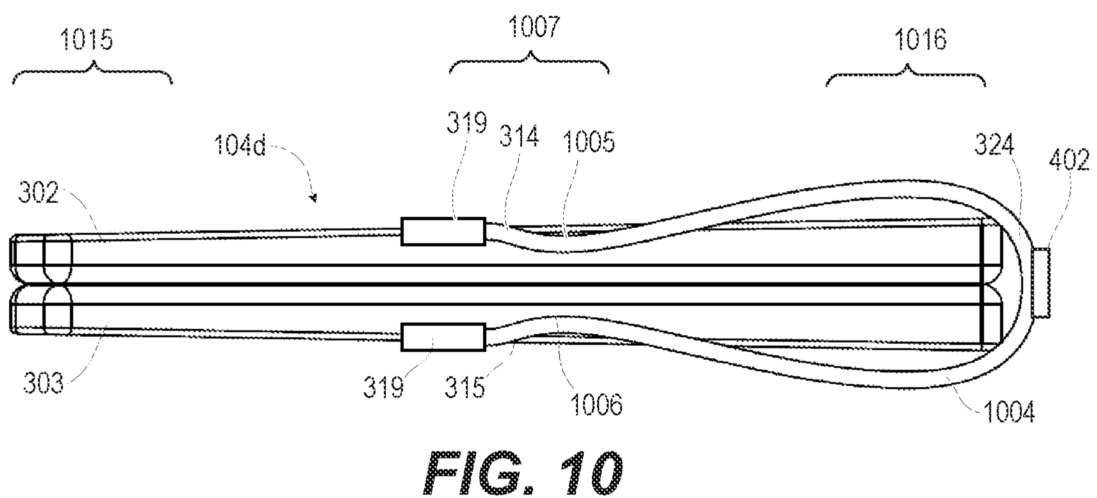
FIG. 10 is a side view of an alternate curved dual side spring V-clip in a closed position and with double bent side springs, according to one or more embodiments.

FIG. 8 is a side view of the example dual side spring V-clip 104*a* of FIG. 5 in a closed position. FIG. 9 is a side view of the example dual side spring V-clip 104*a* of FIG. 5 in a partially open position. FIG. 10 is a side view of an alternate dual side spring V-clip 104*d* in a closed position and with double bent side springs 1004. In a detached, relaxed state, each alternate dual side spring 1004 can comprise crossed distal ends similar to as depicted at 408 of FIG. 4 but differ in having a top reverse bend 1005 distal to first terminal end 314 and a bottom reverse bend 1006 proximal to second terminal end 315 as compared to the proximal bend 324 at a midpoint 1007. The top reverse bend 1005 and the bottom reverse bend 1006 can enable approximately equal force to be applied to both proximal end 1015 and distal end 1016 of the first elongate beam 302 and the second elongate beam 303.

To facilitate an over-molding production method, the ends of the springs should have features to constrain them. The springs could be inserted into the injection molding tool so the beams can be molded and formed around the spring ends. The springs should be constrained from both rotation and axial motion. Shapes that prevent the springs from rotating include at least one flat, a hole through the spring for plastic to flow, a spline, or a swaged section. Additionally, a shape on the spring such as an undercut would constrain the spring in the axial direction.

Figure 11A:
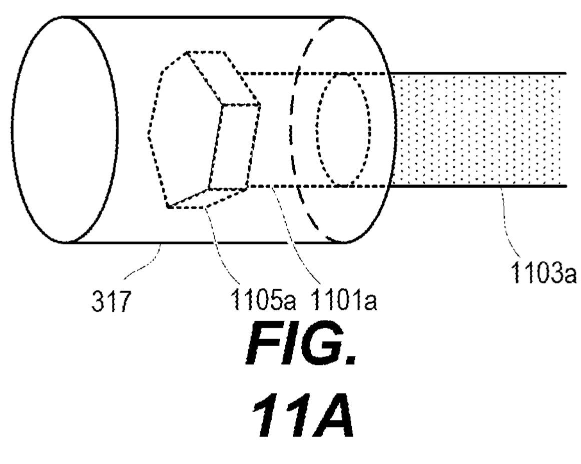
FIG. 11A is a three-dimensional view of spring end having a hexagonal head anti-rotation feature that is encompassed within an overmolded portion of a beam, according to one or more embodiments.
Figure 11B:
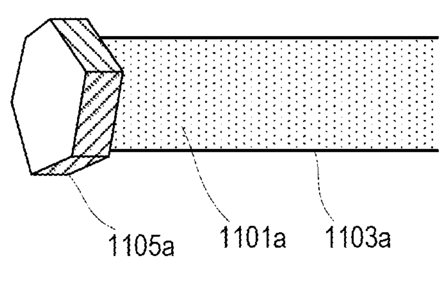
FIG. 11B is a three-dimensional view of the spring end of FIG. 11A, according to one or more embodiments.
Figure 11C:
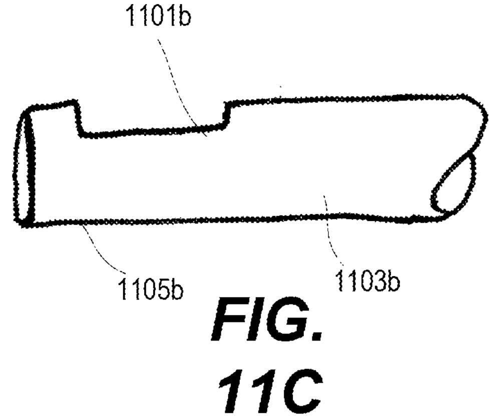
FIG. 11C is a three-dimensional view of an example spring end having an undercut anti-rotation feature, according to one or more embodiments.
Figure 11D:
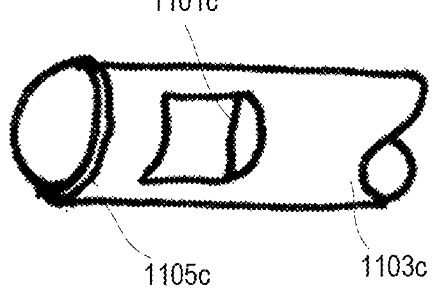
FIG. 11D is a three-dimensional view of an example spring end having a flat anti-rotation feature, according to one or more embodiments.
Figure 11E:
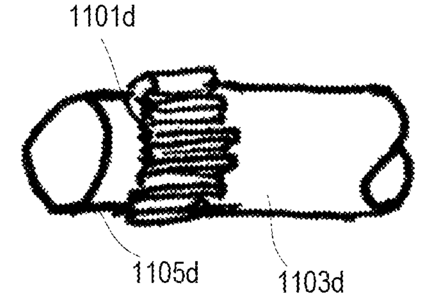
FIG. 11E is a three-dimensional view of an example spring end having a spline anti-rotation feature, according to one or more embodiments.
Figure 11F:
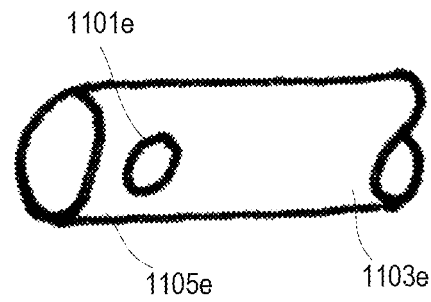
FIG. 11F is a three-dimensional view of an example spring end having a lateral through hole anti-rotation feature, according to one or more embodiments.
Figure 11G:
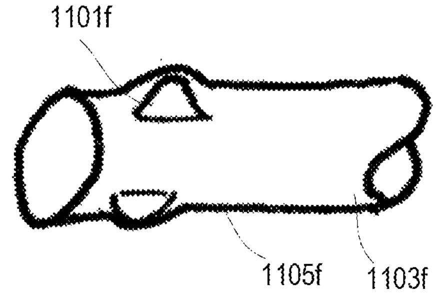
FIG. 11G is a three-dimensional view of an example spring end having a swage anti-rotation feature, according to one or more embodiments.

FIG. 11A is a three-dimensional view of an example spring end 1101*a* of a side spring 1103*a* having an anti-rotation feature 1105*a*, depicted as a hexagonal head, that is encompassed within an overmolded portion 319 of the beam 302 (FIG. 3). FIG. 11B is a three-dimensional view of the spring end 1101*a* of FIG. 11A. FIG. 11C is a three-dimensional view of an example spring end 1101*b* of a side spring 1103*b* having an anti-rotation feature 1105*b*, depicted as an undercut anti-rotation feature. FIG. 11D is a three-dimensional view of an example spring end 1101*c* of a side spring 1103*c* having an anti-rotation feature 1105*c*, depicted as a flat anti-rotation feature. FIG. 11E is a three-dimensional view of an example spring end 1101*d* of a side spring 1103*d* having an anti-rotation feature 1105*d*, depicted as a spline anti-rotation feature. FIG. 11F is a three-dimensional view of an example spring end 1101*e* of a side spring 1103*e* having an anti-rotation feature 1105*e*, depicted as a lateral through hole anti-rotation feature. FIG. 11G is a three-dimensional view of an example spring end 1101*f* of a side spring 1103*f* having an anti-rotation feature 1105*f*, depicted as a swage anti-rotation feature.

Figure 12:
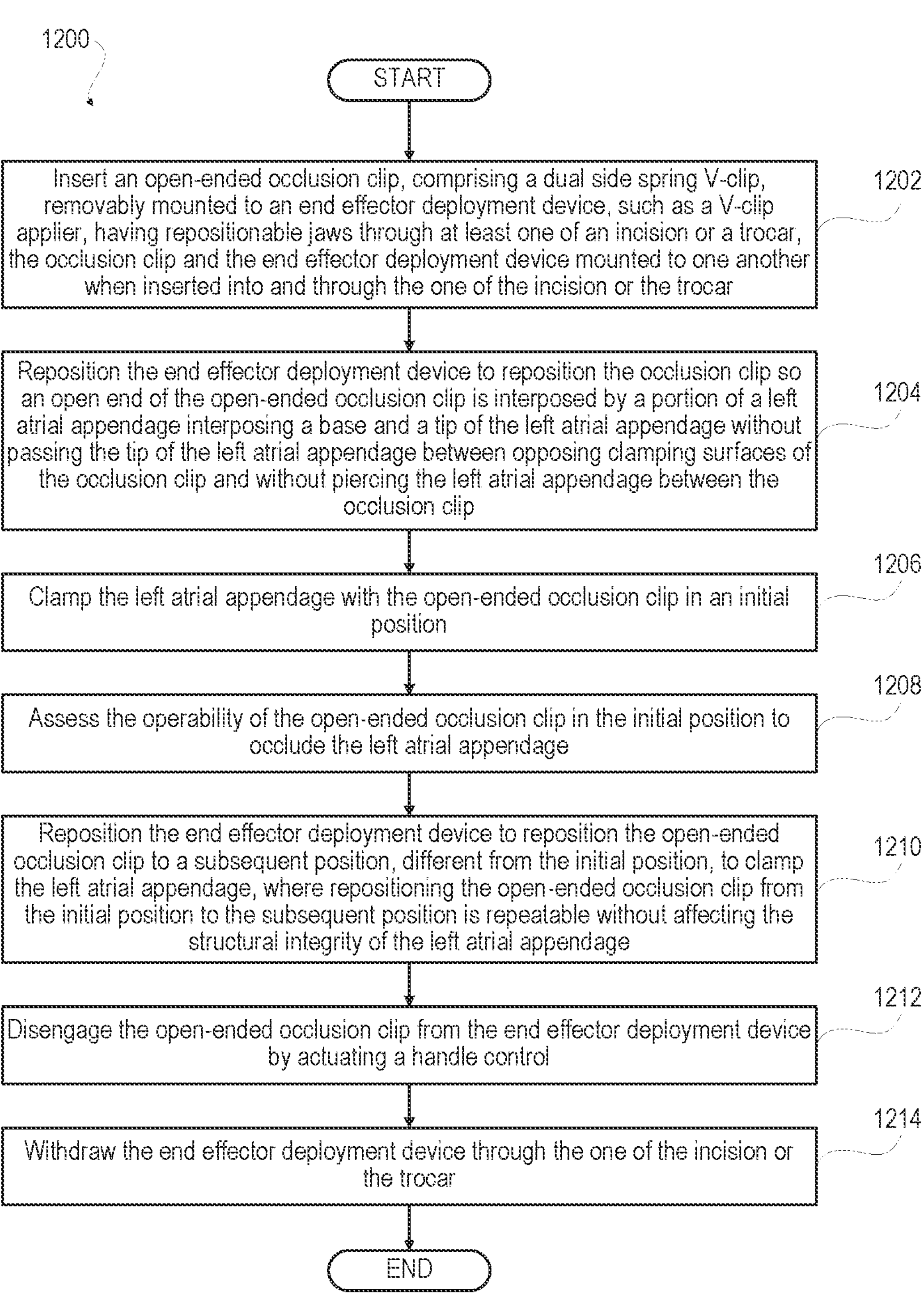
FIG. 12 depicts a flow diagram presenting a method of deploying an occlusion clip, specifically a curved dual side spring V-clip to occlude an LAA, according to one or more embodiments.

FIG. 12 depicts a flow diagram presenting a method 1200 of deploying an occlusion clip, specifically a dual side spring V-clip to occlude an LAA. Components referenced in method 1200 may be identical or similar components described above for FIGS. 1A-1B and 2-8 and 9A-9G and in the documents incorporated by reference herein. Method 1200 can include inserting an open-ended occlusion clip, comprising a dual side spring V-clip, removably mounted to an end effector deployment device, such as a V-clip applier, having repositionable jaws through an incision or a trocar, the occlusion clip and the end effector deployment device mounted to one another when inserted into and through the one of the incision or the trocar (block 1202). Method 1200 can include repositioning the end effector deployment device to reposition the occlusion clip so an open end of the open-ended occlusion clip is interposed by a portion of a left atrial appendage interposing a base and a tip of the left atrial appendage without passing the tip of the left atrial appendage between opposing clamping surfaces of the occlusion clip and without piercing the left atrial appendage between the occlusion clip (block 1204). Method 1200 can include clamping the left atrial appendage with the open-ended occlusion clip in an initial position (block 1206). Method 1200 can include assessing the operability of the open-ended occlusion clip in the initial position to occlude the left atrial appendage (block 1208). Method 1200 can include repositioning the end effector deployment device to reposition the open-ended occlusion clip to a subsequent position, different from the initial position, to clamp the left atrial appendage, where repositioning the open-ended occlusion clip from the initial position to the subsequent position is repeatable without affecting the structural integrity of the left atrial appendage (block 1210). Method 1200 can include disengaging the open-ended occlusion clip from the end effector deployment device by actuating a handle control (block 1212). Method 1200 includes withdrawing the end effector deployment device through the one of the incision or the trocar (block 1214).

In one or more embodiments, a method is provided for deploying an occlusion clip such as a side spring V-clip. The method can include inserting an open-ended occlusion clip removably mounted to an end effector deployment device, having repositionable jaws, through at least one of an incision or a trocar, the open-ended occlusion clip biased to a clamping position. The method can include repositioning the end effector deployment device to counteract a bias of the open-ended occlusion clip and reposition the open-ended occlusion clip to a tissue insertion position where the full bias of the open-ended occlusion clip is not applied to a left atrial appendage tissue. The method can include repositioning the end effector deployment device to reposition the open-ended occlusion clip in the tissue insertion position so a portion of a left atrial appendage between a base and a tip of the left atrial appendage interposes the open-ended occlusion clip without ever having a tip of the left atrial appendage interpose the open-ended occlusion clip. The method can include repositioning the open-ended occlusion clip to apply the full bias to the left atrial appendage.

In a more detailed embodiments, the method can further include inserting the end effector during at least one of an open sternotomy, a left thoracotomy, a right thoracotomy, a left port procedure, a right port procedure, a subxiphoid approach, and a transdiaphragmatic approach. In a further detailed embodiment, the method can include insufflating a thoracic space prior to the inserting end effector. In still a further detailed embodiment, the method can further include making an incision as part of a procedure including at least one of an open sternotomy, a left thoracotomy, a right thoracotomy, a left port procedure, a right port procedure, a subxiphoid approach, and a transdiaphragmatic approach, and introducing a trocar through the incision. In a more detailed embodiment, the end effector deployment device is mounted to a longitudinal conduit, which is mounted to a hand-held device. Repositioning the end effector deployment device can include actuating at least one of a first control and a second control associated with the hand-held device to actively reposition the end effector within at least one of an X-Y plane and a Y-Z plane with respect to the hand-held device. In a more detailed embodiment, the end effector deployment device can be mounted to a longitudinal conduit, which is mounted to a hand-held device. The open-ended occlusion clip can be repositioned from a compressed position to an expanded position prior to interposing a portion of the left atrial appendage between the opposing clamping surfaces. In another more detailed embodiment, the method can further include actuating a handle associated with the hand-held device to direct repositioning of the open-ended occlusion clip between the compressed position and the expanded position. In yet another more detailed embodiment, actuating the handle can cause a pair of jaws associated with the end effector to reposition with respect to one another, and the pair of jaws is mounted to the open-ended occlusion clip. In still another more detailed embodiment, the end effector deployment device can be mounted to a longitudinal conduit, which is mounted to a hand-held device, the method further comprising rotationally repositioning the open-ended occlusion clip with respect to the left atrial appendage by rotating the hand-held device.

In yet another more detailed embodiment, the method can further include grasping the left atrial appendage concurrent with repositioning the end effector deployment device to reposition the occlusion clip so the open end of the open-ended occlusion clip is interposed by the portion of the left atrial appendage. In yet another more detailed embodiment, the method can further include confirming application of the full bias of the open-ended occlusion clip is operative to occlude the left atrial appendage using at least one of visualization and a transesophageal echocardiogram. In a further detailed embodiment, the method can further include disengaging the open-ended occlusion clip from the end effector deployment device, where the end effector deployment device is mounted to a longitudinal conduit, which is mounted to a hand-held device, and disengaging the open-ended occlusion clip from the end effector deployment device includes actuating a control associated with the hand-held device. In still a further detailed embodiment, the control can comprise a repositionable tab operatively coupled to a wire, which is operatively coupled to the end effector and the open-ended occlusion clip, and removing the repositionable tab from the hand-held device repositions the wire with respect to at least one loop encompassing at least one of the open-ended occlusion clip and the end effector deployment device in order to disengage the open-ended occlusion clip from the end effector deployment device. In a more detailed embodiment, the inserting step can include inserting the open-ended occlusion clip and the end effector deployment device through the trocar or the trocar comprises a twelve millimeter or less diameter orifice. In a more detailed embodiment, the end effector deployment device can be mounted to a longitudinal conduit, which is mounted to a hand-held device, and the step of repositioning the end effector deployment device to reposition the open-ended occlusion clip includes locking a position of the end effect deployment device in at least one of an X-Y plane and a Y-Z plane with respect to the hand-held device.

Unless specifically indicated, it will be understood that the description of the structure, function, and/or methodology with respect to any illustrative embodiment herein may apply to any other illustrative embodiments. More generally, it is within the scope of the present disclosure to utilize any one or more features of any one or more example embodiments described herein in connection with any other one or more features of any other one or more other example embodiments described herein. Accordingly, any combination of any of the features or embodiments described herein is within the scope of this disclosure.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

While the innovation has been described with reference to exemplary embodiments, it will be understood by those skilled in the art that various changes may be made, and equivalents may be substituted for elements thereof without departing from the scope of the innovation. In addition, many modifications may be made to adapt a particular system, device, or component thereof to the teachings of the innovation without departing from the essential scope thereof. Therefore, it is intended that the innovation not be limited to the particular embodiments disclosed for carrying out this innovation, but that the innovation will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the innovation. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present innovation has been presented for purposes of illustration and description but is not intended to be exhaustive or limited to the innovation in the form disclosed. Many modifications and variations will be apparent to those of ordinary skill in the art without departing from the scope and spirit of the innovation. The embodiments were chosen and described in order to best explain the principles of the innovation and the practical application, and to enable others of ordinary skill in the art to understand the innovation for various embodiments with various modifications as are suited to the particular use contemplated.

What is claimed is:

1. An apparatus comprising:

a first elongate beam having a straight proximal portion and laterally curved distal portion;

a second elongate beam that matches the first elongate beam and positionable between a closed state in parallel alignment with the first elongate beam and an open state being distally angled away from the first elongate beam in a V-shape;

a dual side spring assembly configured to urge the first and the second elongate beams from the open state to the closed state and comprising a right-side spring and a left-side spring having first and second terminal ends attached to distal sections respectively of the first and the second elongate beams and extending proximally to a respective proximal bend, wherein each of the right and the left-side springs in a free state present crossed distal ends having a reverse bend as compared to the proximal bend, the right-side spring and the left-side spring having separated distal ends as attached to the first and the second elongate beams; and a lateral spacing element attached between respective proximal bends of the right-side spring and the left-side spring that maintains parallel alignment to resist lateral splaying movement of the first and second elongate beams.

2. The apparatus of claim 1, wherein each of the first and second terminal ends of the right-side and left-side springs comprise an overmolded tip that is attached to corresponding distal sections of the first and the second elongate beams.

3. The apparatus of claim 2, wherein the overmolded tip comprises anti-rotation feature that comprises one or more of a polygonal head, an undercut portion, a flat portion, a spline portion, a hole, and a swage.

4. The apparatus of claim 1, wherein:

the first and the second terminal ends of the right-side spring are vertically aligned at a first longitudinal position on right-sides respectively of the first and the second elongate beams; and the first and the second terminal ends of the left-side spring are vertically aligned at the first longitudinal position on left-sides respectively of the first and the second elongate beams, the second longitudinal position longitudinally spaced from the first longitudinal position, the right and left-side springs being identically sized.

5. The apparatus of claim 1, wherein:

the first and the second terminal ends of the right-side spring are vertically aligned at a first longitudinal position on right-sides respectively of the first and the second elongate beams; and the first and the second terminal ends of the left-side spring are vertically aligned at a second longitudinal position on left-sides respectively of the first and the second elongate beams, the second longitudinal position longitudinally spaced from the first longitudinal position, the right and left-side springs differently longitudinally sized.

6. The apparatus of claim 1, wherein the first and the second elongate beams present atraumatic inward surfaces.

7. The apparatus of claim 1, further comprising one or more materials compatible with surgical implantation on a left atrial appendage of a heart of a patient.

8. The apparatus of claim 1, wherein the lateral spacing element is proximal to the first elongate beam and the second elongate beam.

9. An apparatus comprising:

a first elongate beam having a straight proximal portion and laterally curved distal portion that defines a concave lateral side and a convex lateral side;

a second elongate beam that matches the first elongate beam and positionable between a closed state in parallel alignment with the first elongate beam and an open state being distally angled away from the first elongate beam in a V-shape;

a right-side spring having a first cross sectional dimension and having first and second terminal ends attached to distal sections respectively of the first and the second elongate beams and extending proximally to a respective proximal bend;

a left-side spring having a second cross sectional dimension that is different from the first cross sectional dimension and having first and second terminal ends attached to distal sections respectively of the first and the second elongate beams and extending proximally to a respective proximal bend, one of the right-side spring and the left-side spring having a larger one of the first and the second cross sectional dimension being on the concave lateral side wherein each of the right-side spring and the left-side spring in a free state present crossed distal ends having a reverse bend as compared to the proximal bend, the right-side spring and the left-side spring having separated distal ends as attached to the first and the second elongate beams.

10. The apparatus of claim 9, wherein each of the first and second terminal ends of the right-side and left-side springs comprise an overmolded tip that is attached to corresponding distal sections of the first and the second elongate beams.

11. The apparatus of claim 10, wherein the overmolded tip comprises anti-rotation feature that comprises one or more of a polygonal head, an undercut portion, a flat portion, a spline portion, a hole, and a swage.

12. The apparatus of claim 9, wherein:

the first and the second terminal ends of the right-side spring are vertically aligned at a first longitudinal position on right-sides respectively of the first and the second elongate beams; and the first and the second terminal ends of the left-side spring are vertically aligned at the first longitudinal position on left-sides respectively of the first and the second elongate beams, the second longitudinal position longitudinally spaced from the first longitudinal position, the right and left-side springs being identically sized.

13. The apparatus of claim 9, wherein:

the first and the second terminal ends of the right-side spring are vertically aligned at a first longitudinal position on right-sides respectively of the first and the second elongate beams; and the first and the second terminal ends of the left-side spring are vertically aligned at a second longitudinal position on left-sides respectively of the first and the second elongate beams, the second longitudinal position longitudinally spaced from the first longitudinal position, the right and left-side springs differently longitudinally sized.

14. The apparatus of claim 9, wherein the first and the second elongate beams present atraumatic inward surfaces.

15. The apparatus of claim 9, further comprising one or more materials compatible with surgical implantation on a left atrial appendage of a heart of a patient.

16. The apparatus of claim 9, further comprising a lateral spacing element proximal to the first elongate beam and the second elongate beam.

* * * * *